United States Patent
Soji et al.

(10) Patent No.: US 12,282,300 B2
(45) Date of Patent: Apr. 22, 2025

(54) INFORMATION PROCESSING APPARATUS, SYSTEM, NON-TRANSITORY COMPUTER-READABLE STORAGE MEDIUM WITH EXECUTABLE PROGRAM STORED THEREON, AND METHOD

(71) Applicant: Nintendo Co., Ltd., Kyoto (JP)

(72) Inventors: Hiroki Soji, Kyoto (JP); Hirosuke Kinoshita, Kyoto (JP)

(73) Assignee: Nintendo Co., Ltd., Kyoto (JP)

( * ) Notice: Subject to any disclaimer, the term of this patent is extended or adjusted under 35 U.S.C. 154(b) by 435 days.

(21) Appl. No.: 17/863,606

(22) Filed: Jul. 13, 2022

(65) Prior Publication Data

US 2023/0085095 A1  Mar. 16, 2023

(30) Foreign Application Priority Data

Sep. 16, 2021 (JP) ................. 2021-150869

(51) Int. Cl.
*G04G 21/02* (2010.01)
*A61B 5/00* (2006.01)
*G04G 13/02* (2006.01)

(52) U.S. Cl.
CPC ......... *G04G 21/025* (2013.01); *A61B 5/4812* (2013.01); *G04G 13/02* (2013.01)

(58) Field of Classification Search
CPC ..... G04G 21/025; G04G 13/02; A61B 5/4812

USPC ........................................................ 340/575
See application file for complete search history.

(56) References Cited

U.S. PATENT DOCUMENTS

| | | | |
|---|---|---|---|
| 10,568,565 B1 * | 2/2020 | Kahn | A61B 5/1126 |
| 11,963,792 B1 * | 4/2024 | Kahn | A61B 5/4812 |
| 2009/0231964 A1 * | 9/2009 | Kraft | G04G 13/026 |
| | | | 368/250 |
| 2015/0258301 A1 * | 9/2015 | Trivedi | A61B 5/0024 |
| | | | 600/28 |
| 2018/0059625 A1 * | 3/2018 | Yang | G04G 13/026 |

FOREIGN PATENT DOCUMENTS

JP  2017-106872  6/2017

* cited by examiner

*Primary Examiner* — Kerri L McNally
(74) *Attorney, Agent, or Firm* — Nixon & Vanderhye PC

(57) ABSTRACT

An information processing apparatus includes sound selection means for selecting a sound to be outputted from a sound candidate group, sound output means for outputting the selected sound when an output condition is satisfied, sleep state estimation means for estimating a sleep state of a user based on a result of measurement by a sensor that measures body motion of the user, hours-of-sleep calculation means for calculating hours of sleep of the user based on the estimated sleep state of the user, and addition means for adding a new sound to the sound candidate group based on the calculated hours of sleep of the user.

27 Claims, 16 Drawing Sheets

FIG.7

| NUMBER | CUMULATIVE TOTAL OF HOURS OF SLEEP | |
|---|---|---|
| 1 | 10hr | ← ADDITION OF SOUND |
| 2 | 20hr | ← ADDITION OF SOUND |
| 3 | 40hr | ← ADDITION OF SOUND |
| 4 | 80hr | ← ADDITION OF SOUND |
| 5 | 200hr | ← ADDITION OF SOUND |
| 6 | 500hr | ← ADDITION OF SOUND |
| 7 | 1000hr | ← ADDITION OF SOUND |
| ... | ... | ← ADDITION OF SOUND |

FIG.12

| MOOD | LONG | NORMAL | SHORT | CANDIDATE |
|---|---|---|---|---|
| FAWNING | ✓ | ✓ | | ADDED |
| FINE_1 | ✓ | ✓ | ✓ | ADDED |
| FINE_2 | ✓ | | | |
| GRUMPY_1 | ✓ | ✓ | | ADDED |
| GRUMPY_2 | ✓ | ✓ | ✓ | ADDED |
| SLEEPY_1 | ✓ | ✓ | ✓ | ADDED |
| SLEEPY_2 | ✓ | | | |

FIG.13

| MOOD | LONG | NORMAL | SHORT | CANDIDATE |
|---|---|---|---|---|
| FAWNING | 2 | 1 | 2 | ADDED |
| FINE_1 | 3 | 2 | 1 | ADDED |
| FINE_2 | 3 | 2 | 1 | |
| GRUMPY_1 | 1 | 2 | 3 | ADDED |
| GRUMPY_2 | 1 | 2 | 3 | ADDED |
| SLEEPY_1 | 1 | 1 | 3 | ADDED |
| SLEEPY_2 | 1 | 1 | 3 | |

FIG.14

| | MOOD | LONG | NORMAL | SHORT | CANDIDATE |
|---|---|---|---|---|---|
| 132-1 | FAWNING | 2 | 1 | 0 | ADDED |
| 132-2 | FINE_1 | 3 | 2 | 1 | ADDED |
| 132-3 | FINE_2 | 3 | 0 | 0 | |
| 132-4 | GRUMPY_1 | 1 | 2 | 3 | ADDED |
| 132-5 | GRUMPY_2 | 1 | 2 | 3 | ADDED |
| 132-6 | SLEEPY_1 | 1 | 0 | 0 | ADDED |
| 132-7 | SLEEPY_2 | 1 | 0 | 0 | |

INFORMATION PROCESSING APPARATUS, SYSTEM, NON-TRANSITORY COMPUTER-READABLE STORAGE MEDIUM WITH EXECUTABLE PROGRAM STORED THEREON, AND METHOD

This nonprovisional application claims priority to Japanese Patent Application No. 2021-150869 filed with the Japan Patent Office on Sep. 16, 2021, the entire contents of which are hereby incorporated by reference.

FIELD

The present disclosure relates to an information processing apparatus and a system that estimate a sleep state, a medium having a program directed to the information processing apparatus stored thereon, and a method performed in the information processing apparatus.

BACKGROUND AND SUMMARY

An apparatus that more diversifies messages and characters to be outputted in response to an operation by a user has been known. For example, an alarm clock that performs processing for increasing an empirical value when an operation to stop an alarm is performed at the time of sounding of the alarm or an operation to stop the alarm is performed at the time of sounding again of the alarm once stopped by a snooze function and processing for increasing variation in messages to be outputted as a prescribed empirical value is attained and a level is raised has been disclosed.

In the conventional apparatus described above, estimation of a sleep state of a user is not assumed. The present disclosure is directed to a scheme that allows various sounds to be provided to a user based on a sleep state of the user.

An exemplary embodiment provides an information processing apparatus that includes a memory storing a computer-readable program and one or more processors. The one or more processors, when executing the computer-readable program, perform selecting a sound to be outputted from a sound candidate group, outputting the selected sound when an output condition is satisfied, estimating a sleep state of a user based on a result of measurement by a sensor that measures body motion of the user, calculating hours of sleep of the user based on the estimated sleep state of the user, and adding a new sound to the sound candidate group based on the calculated hours of sleep of the user.

According to this configuration, the information processing apparatus calculates the hours of sleep of the user based on the estimated sleep state of the user and adds the new sound to the sound candidate group based on the calculated hours of sleep of the user. Therefore, in order to increase variation in sounds to be outputted, the user has to have a sleep. In other words, the user can be motivated to have more sleep in association with output of the new sound.

The adding the new sound to the sound candidate group may be based on a cumulative total of the calculated hours of sleep of the user. According to this configuration, since the new sound is added based on the cumulative total of the hours of sleep of the user, the user can be motivated to have a sleep as long as possible.

The adding the new sound to the sound candidate group may include adding the new sound when a cumulative total of the calculated hours of sleep of the user reaches a prescribed threshold value. According to this configuration, a developer can freely adjust at which timing a sound is to be added.

The prescribed threshold value may include a plurality of threshold values. In this case, the adding the new sound to the sound candidate group may include adding the new sound each time the cumulative total of the calculated hours of sleep of the user reaches at least one of the plurality of threshold values. According to this configuration, a sound can be added stepwise with the use of the plurality of threshold values.

As compared with a difference between a first threshold value included in the plurality of threshold values and a second threshold value largest next to the first threshold value, a difference between the second threshold value and a third threshold value largest next to the second threshold value may be larger. According to this configuration, since a sound is soon added immediately after start of use, the user can use the information processing apparatus with enjoyment. In addition, since a time period until addition of all sounds can be longer, the user can use the information processing apparatus with enjoyment for a longer period of time.

The one or more processors, when executing the computer-readable program, may further perform, after the user wakes up, evaluation based on the calculated hours of sleep immediately before. In this case, the adding the new sound to the sound candidate group may include adding the new sound based on a result of the evaluation. According to this configuration, by evaluating after wake-up of the user, the hours of sleep of the user based on the calculated hours of sleep immediately before, a condition for adding the new sound can appropriately be determined.

The adding the new sound to the sound candidate group may include determining the new sound to be added by a draw. According to this configuration, since the user is unable to expect the new added sound, the user can be given expectation and can more strongly be motivated to have a sleep.

A probability that each of sounds that have not yet been added to the sound candidate group is determined as the new sound may be equal. According to this configuration, since a sound that has not yet been added to the sound candidate group is selected at the same probability and added to the sound candidate group, variation in sounds to be outputted can be increased without any bias being given to a specific sound.

The one or more processors, when executing the computer-readable program, may further perform determining whether or not to activate processing for adding the new sound to the sound candidate group based on the calculated hours of sleep of the user. In this case, the adding the new sound to the sound candidate group may include adding the new sound to the sound candidate group when processing for adding the new sound is activated. According to this configuration, since it is not necessarily the case that the new sound is added without fail based on the calculated hours of sleep of the user, the user can be given expectation. Since determination not to add the new sound may be made, the user can be motivated to have a sleep.

The selecting a sound may include selecting a sound to be outputted from the sound candidate group by a draw. According to this configuration, since a sound to be outputted from an output apparatus is varied by the draw, the user can be given expectation.

A probability that a sound included in the sound candidate group is selected as a sound to be outputted by the draw may be higher as the hours of sleep of the user immediately before the output condition is satisfied are longer. According to this configuration, since a sound that is more likely to be outputted is varied based on the hours of sleep of the user, the user can be motivated to have a sleep for output of more types of sounds.

The selecting the sound may include selecting, when the calculated hours of sleep of the user exceed prescribed hours, a sound to be outputted from among more sounds than when the calculated hours of sleep of the user do not exceed the prescribed hours. According to this configuration, since the output apparatus outputs more types of sounds as the hours of sleep are longer, the user can be motivated to have a sleep.

A probability that at least one sound included in the sound candidate group is selected as the sound to be outputted may be higher as the hours of sleep of the user are longer. According to this configuration, since a probability of selection of a specific sound included in the sound candidate group remains low unless the hours of sleep are long, the user can be motivated to have a sleep.

A probability that each of sounds included in the sound candidate group is selected as the sound to be outputted may be equal. According to this configuration, sounds included in the sound candidate group can evenly be outputted.

A sound more recently added to the sound candidate group may be higher in probability of selection as the sound to be outputted. According to this configuration, since a newly added sound is more likely to be outputted as the user has a sleep, the user can more reliably feel an effect of having a sleep.

The selecting a sound may include selecting the sound to be outputted in a predetermined order from the sound candidate group. According to this configuration, since sounds included in the sound candidate group are sequentially outputted, each sound can reliably be heard by the user.

A sound may be added to the sound candidate group in a unit of a sound set composed of a plurality of sounds. In this case, the selecting a sound may include selecting sounds to be outputted in the unit of the sound set and determining a sound to be outputted from among the sounds included in the selected sound set. According to this configuration, since switching of output between sounds included in the selected sound set can be made, variation in sounds to be outputted can be increased.

The selecting the sound may include selecting as a sound to be outputted next, a sound different from a previously selected sound from among sounds included in the sound set when a switching condition is satisfied after output of the sound is started. According to this configuration, a sound included in the selected sound set can be heard by the user.

The switching condition may include a condition that a duration of output of a sound that is currently being outputted reaches a prescribed duration. According to this configuration, since switching to output of a next sound is made when the same sound is outputted for the duration of output, the user can enjoy various sounds.

The one or more processors, when executing the computer-readable program, may further perform temporarily stopping output of the sound. In this case, the switching condition may include temporary stop of output of the sound. According to this configuration, when output of the sound is temporarily stopped, a sound to be outputted next is different from the previous sound. Therefore, the user can enjoy various sounds.

The outputting the sound may include outputting again the sound, output of which has ended, when a condition for output again is satisfied within a prescribed period after end of output of the sound. According to this configuration, even when the user missed a sound outputted at the time when the output condition was satisfied or when the user was unable to sufficiently hear the sound, the user can hear the same sound later.

The one or more processors, when executing the computer-readable program, may further perform sensing a shake that occurs in the information processing apparatus. In this case, the condition for output again may include sensing of the shake of the information processing apparatus. According to this configuration, since the sound is outputted again as the user shakes the information processing apparatus, the user can hear the sound again by an easy operation.

In the information processing apparatus, the sensor may be an acceleration sensor. According to this configuration, the sleep state of the user can be estimated with the use of the acceleration sensor.

The one or more processors, when executing the computer-readable program, may further perform obtaining a sound from another information processing apparatus different from the information processing apparatus. According to this configuration, variation in sounds outputted from the output apparatus can be increased by obtaining a sound from another information processing apparatus.

Another exemplary embodiment provides a system including a sound generator. The system includes a sound selection module that selects a sound to be outputted from a sound candidate group, a sound output module that outputs the selected sound from the sound generator when an output condition is satisfied, a sleep state estimation module that estimates a sleep state of a user based on a result of measurement by a sensor that measures body motion of the user, an hours-of-sleep calculation module that calculates hours of sleep of the user based on the estimated sleep state of the user, and an addition module that adds a new sound to the sound candidate group based on the calculated hours of sleep of the user.

Another exemplary embodiment provides a non-transitory computer-readable storage medium with an executable program stored thereon. The program causes a computer configured to output a sound to perform selecting a sound to be outputted from a sound candidate group, outputting the selected sound when an output condition is satisfied, estimating a sleep state of a user based on a result of measurement by a sensor that measures body motion of the user, calculating hours of sleep of the user based on the estimated sleep state of the user, and adding a new sound to the sound candidate group based on the calculated hours of sleep of the user.

Another exemplary embodiment provides a method performed in an information processing apparatus configured to output a sound. The method includes selecting a sound to be outputted from a sound candidate group, outputting the selected sound when an output condition is satisfied, estimating a sleep state of a user based on a result of measurement by a sensor that measures body motion of the user, calculating hours of sleep of the user based on the estimated sleep state of the user, and adding a new sound to the sound candidate group based on the calculated hours of sleep of the user.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 7 shows an exemplary illustrative non-limiting drawing illustrating an exemplary condition used in the sound addition processing according to the present embodiment.

FIG. 12 shows an exemplary illustrative non-limiting drawing illustrating an exemplary method of determining selectable sounds in the output apparatus according to the present embodiment.

FIG. 13 shows an exemplary illustrative non-limiting drawing illustrating an exemplary method of selecting a sound in the output apparatus according to the present embodiment.

FIG. 14 shows an exemplary illustrative non-limiting drawing illustrating another exemplary method of selecting a sound in the output apparatus according to the present embodiment.

DETAILED DESCRIPTION OF NON-LIMITING EXAMPLE EMBODIMENTS

Figure 1:
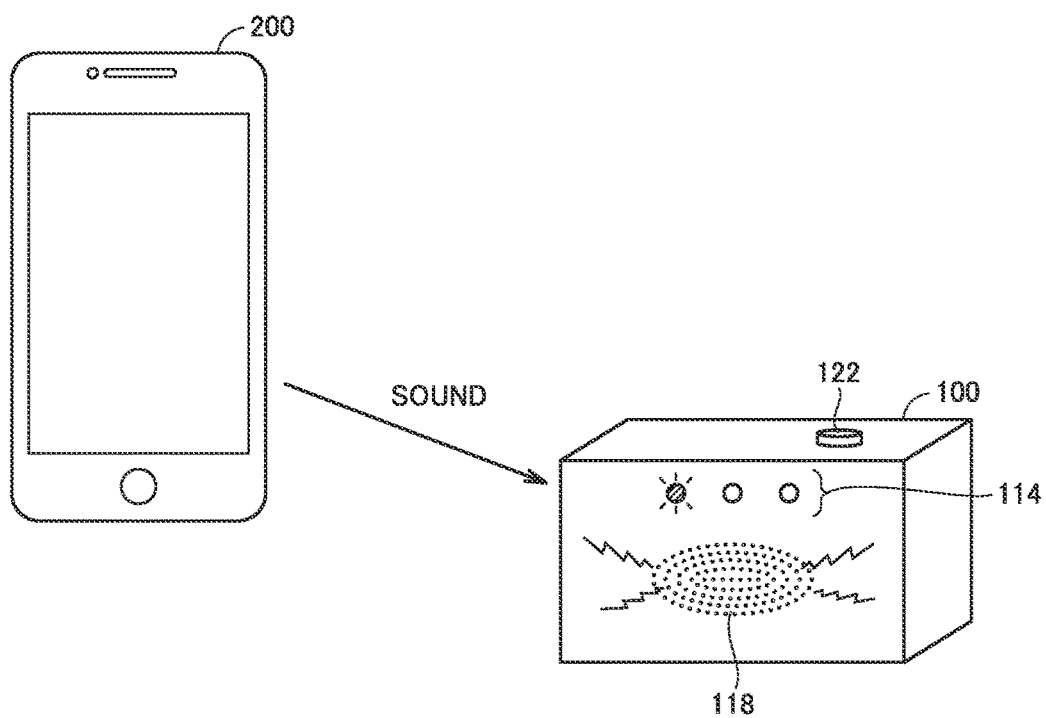
FIG. 1 shows an exemplary illustrative non-limiting drawing illustrating an overall configuration of a system according to the present embodiment.

The present embodiment will be described in detail with reference to the drawings. The same or corresponding elements in the drawings have the same reference characters allotted and description thereof will not be repeated.

A. Exemplary Overall Configuration

An exemplary overall configuration of a system 1 according to the present embodiment will initially be described.

FIG. 1 is a schematic diagram showing an overall configuration of system 1 according to the present embodiment.

Referring to FIG. 1, system 1 includes an output apparatus 100 by way of example of an information processing apparatus configured to output a sound. Output apparatus 100 may be configured as a kind of an alarm clock.

System 1 may further include a portable terminal 200 that can exchange data by wireless or wired communication with output apparatus 100. Portable terminal 200, however, is not an essential feature.

Portable terminal 200 may be an information processing apparatus configured to execute any applications. Portable terminal 200 is implemented, for example, by a smartphone, a tablet, a personal computer, or a game device. Portable terminal 200 can also transmit one or more sounds to output apparatus 100 in accordance with an operation by a user.

When output apparatus 100 and portable terminal 200 are connected to each other through wireless communication, for example, any wireless scheme such as Bluetooth®, ZigBee®, wireless LAN (IEEE 802.11), or infrared communication can be adopted.

B. Exemplary Hardware Configuration of Output Apparatus 100

An exemplary hardware configuration of output apparatus 100 of system 1 according to the present embodiment will now be described.

Figure 2:
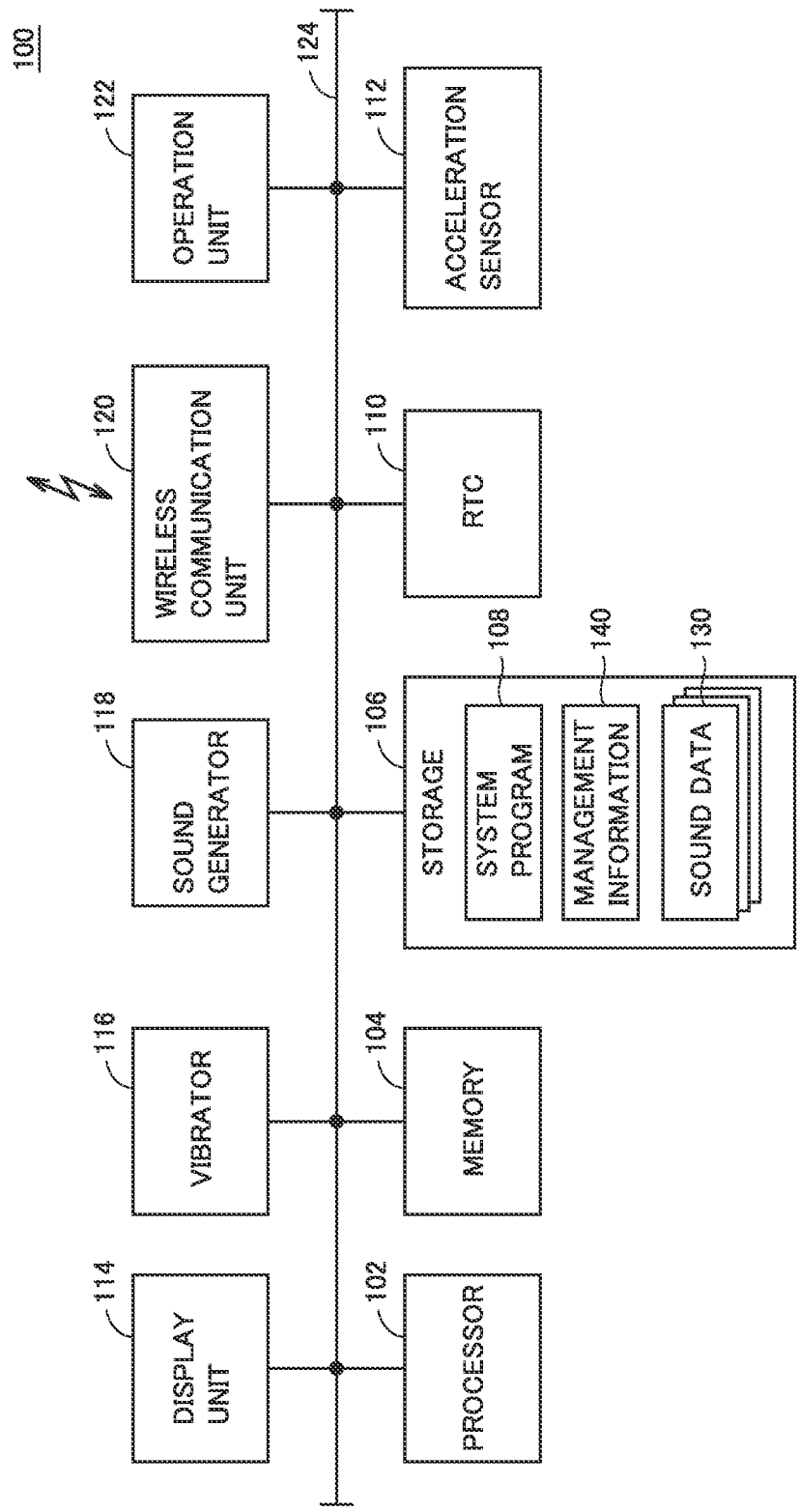
FIG. 2 shows an exemplary illustrative non-limiting drawing illustrating a hardware configuration of an output apparatus in the system according to the present embodiment.

FIG. 2 is a schematic diagram showing a hardware configuration of output apparatus 100 in system 1 according to the present embodiment. Referring to FIG. 2, output apparatus 100 represents an exemplary computer, and includes, as its main components, one or more processors 102, a memory 104, a storage 106, a real time clock (RTC) 110, an acceleration sensor 112, a display unit 114, a vibrator 116, a sound generator 118, a wireless communication unit 120, and an operation unit 122. These components are electrically connected to one another through a bus 124.

Processor 102 is a processing entity (processing means) for performing processing provided by output apparatus 100. Processor 102 performs processing as will be described later by reading a system program 108 stored in storage 106 and developing the system program on memory 104. System program 108 includes an instruction code for performing processing as will be described later.

Memory 104 is a storage device that can be accessed by processor 102, and it is implemented, for example, by a volatile storage device such as a dynamic random access memory (DRAM) or a static random access memory (SRAM). Storage 106 is implemented, for example, by a non-volatile storage device such as a flash memory.

In storage 106, sound data 130 and a sound management table 140 are stored in addition to system program 108.

RTC 110 manages time and provides information indicating current time to processor 102 or the like.

Acceleration sensor 112 is a sensor that detects motion produced in output apparatus 100 and used for estimation of a sleep state of a user as will be described later.

Display unit 114 is a component that visually provides information to a user, and it is implemented, for example, by a light emitting diode (LED) or a liquid crystal display.

Vibrator 116 provides vibration to a user.

Sound generator 118 is a component that provides any auditory information to a user, and it is implemented, for example, by a speaker or a buzzer.

Wireless communication unit 120 exchanges data with portable terminal 200 through a wireless signal.

Operation unit 122 is a component that accepts an operation from a user, and it is implemented by such a device as a push button, a control lever, a touch panel, a mouse, and the like.

Processing performed in output apparatus 100 may be performed by execution of a program by the processor, or a part or the entirety thereof may be implemented by hard-wired circuitry such as an application specific integrated circuit (ASIC) or a field programmable gate array (FPGA).

The term "processor" herein encompasses not only a normal meaning of a processing circuit that performs processing in accordance with an instruction code described in a program, such as a central processing unit (CPU), a micro processing unit (MPU), or a graphics processing unit (GPU), but also hard-wired circuitry such as an ASIC or an FPGA. In the hard-wired circuitry such as an ASIC or an FPGA, a circuit corresponding to processing to be executed is formed in advance. Furthermore, the "processor" herein also encompasses circuitry in which a plurality of functions are integrated, such as a system on chip (SoC).

C. Overview of Processing

Overview of processing in output apparatus 100 according to the present embodiment will now be described. Output apparatus 100 performs sound addition processing for adding a new sound to a sound candidate group based on hours of sleep of a user and sound selection and output processing for selecting a sound to be outputted from a sound candidate group and outputting the selected sound when an output condition is satisfied.

"Hours of sleep" herein means a length of time for which a user is asleep and/or is estimated to be asleep. A unit for calculating "hours of sleep" is arbitrarily defined, for example, as hour, minute, second, and so on.

Output apparatus 100 according to the present embodiment can output a plurality of sounds. In the description below, an example in which sounds are categorized based on an attribute "mood" is shown. Specifically, a plurality of sounds corresponding to a plurality of moods, respectively, are prepared. By preparing sounds in consideration of such "moods", a user can feel output apparatus 100 as if it were a "living creature." The user thus tends to feel an attachment to output apparatus 100. Any type of sounds may be prepared and outputted.

The "sound" herein collectively refers to an expression that a user can perceive by the sense of hearing. The term "sound" means a unit of output from output apparatus 100, and whether or not a "sound" is to be outputted from output apparatus 100 is managed for each "sound".

"Sound data" herein means music data for realizing output of a sound. For example, the sound data is composed of data coded under a known music format.

A "sound set" herein means a set of a plurality of "sounds". In other words, the "sound set" is composed of a plurality of "sounds". For example, a "sound set" may be composed of a plurality of "sounds" common or similar in attribute.

A "sound candidate group" herein means a set of sounds output of which from output apparatus 100 is logically permitted. A plurality of sounds are prepared in advance for output apparatus 100, and output apparatus 100 changes one or all of the plurality of these prepared sounds to an available state based on hours of sleep of a user. A sound may be added to the "sound candidate group" in a unit of a sound set.

Figure 3:
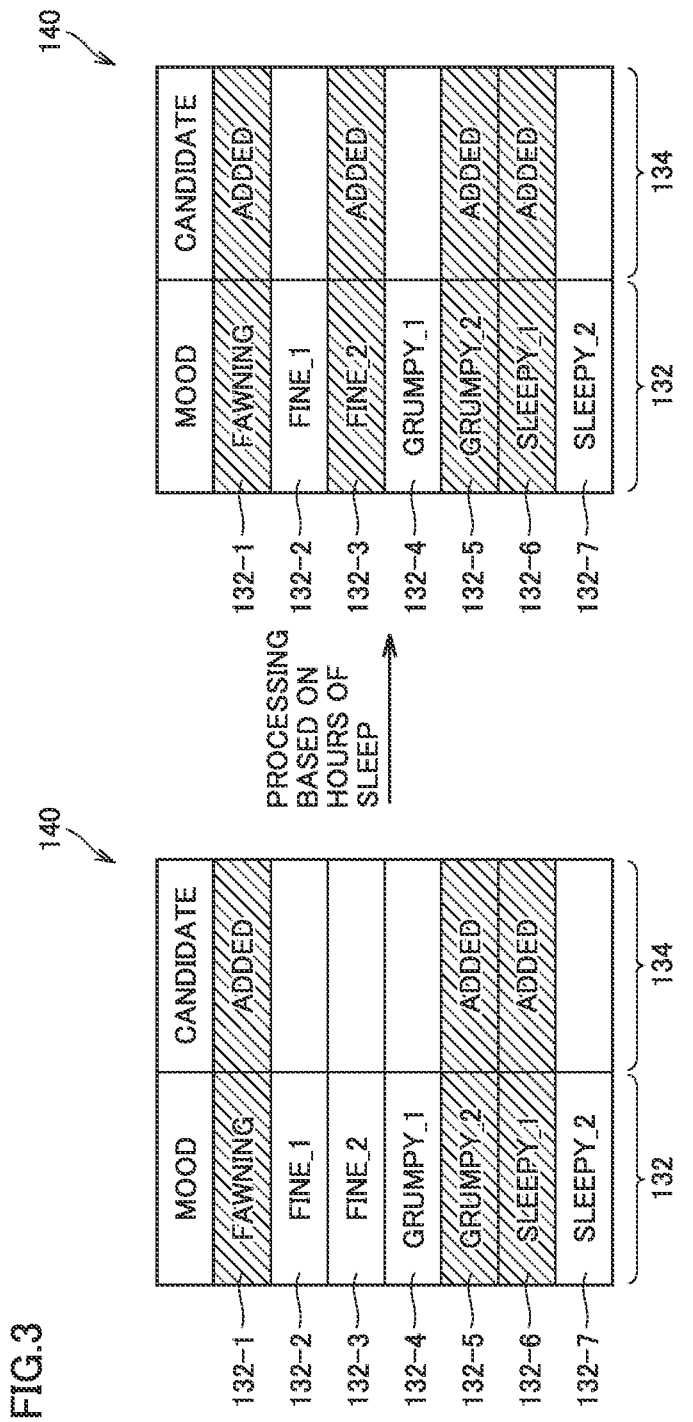
FIG. 3 shows an exemplary illustrative non-limiting drawing illustrating sound addition processing according to the present embodiment.

FIG. 3 is a schematic diagram for illustrating sound addition processing according to the present embodiment. Referring to FIG. 3, sound management table 140 includes information on a prepared sound 132 and information as to whether or not each sound 132 has already been added to a sound candidate group 134.

For output apparatus 100, for example, sounds 132-1 to 132-7 (which may also collectively be referred to "sound 132" below) corresponding to respective moods are prepared. Each sound 132 is brought in correspondence with specific sound data 130.

An element in the sound candidate group may be a sound set composed of a plurality of sounds 132, rather than an individual sound 132. One or more sounds 132 included in the sound set each correspond to the same "mood". Details of the sound set will be described later.

In an initial state, at least one of the plurality of sounds 132 is available. In other words, at least one sound 132 has already been added to sound candidate group 134.

Output apparatus 100 adds at least one of sounds 132 that have not yet been added to sound candidate group 134 among sounds 132 prepared in advance to sound candidate group 134, based on hours of sleep of the user. Details of processing (sound addition processing) for adding sound 132 to sound candidate group 134 will be described later.

Figure 4A:
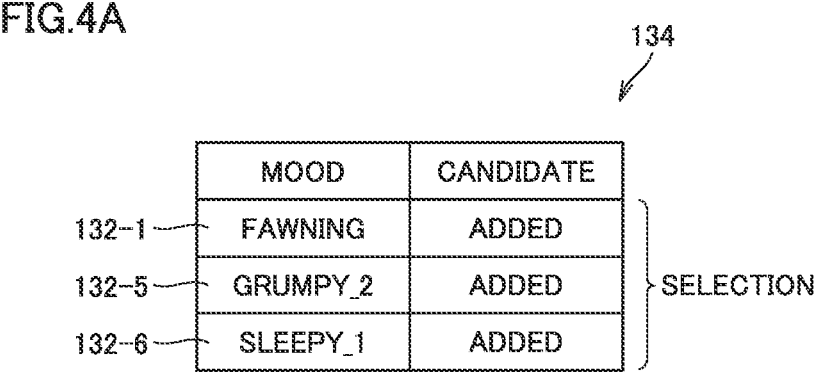
FIGS. 4A and 4B show exemplary illustrative non-limiting drawings illustrating sound selection and output processing according to the present embodiment.
Figure 4B:
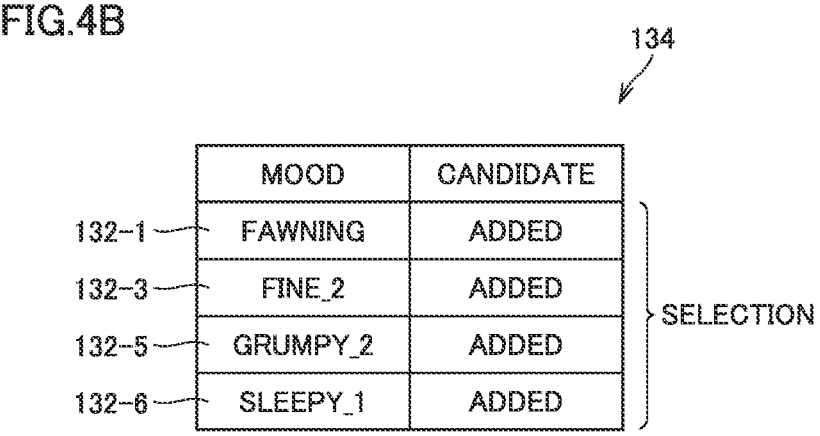

FIGS. 4A and 4B are schematic diagrams for illustrating sound selection and output processing according to the present embodiment. Referring to FIG. 4, output apparatus 100 selects sound 132 to be outputted from sound candidate group 134. Output apparatus 100 outputs the selected sound when an output condition is satisfied.

Sound candidate group 134 shown in FIG. 4A includes sounds 132-1, 132-5, and 132-6. Therefore, output apparatus 100 selects one sound 132 from these three sounds 132.

Sound candidate group 134 shown in FIG. 4B is in a state where sound 132-3 has been added to sound candidate group 134 by sound addition processing. In other words, sound candidate group 134 includes sounds 132-1, 132-3, 132-5, and 132-6. Therefore, output apparatus 100 selects one sound 132 from these four sounds 132.

Output apparatus 100 may perform only one of sound addition processing and sound selection and output processing.

D. Exemplary Functional Configuration

An exemplary functional configuration of output apparatus 100 according to the present embodiment will now be described.

Figure 5:
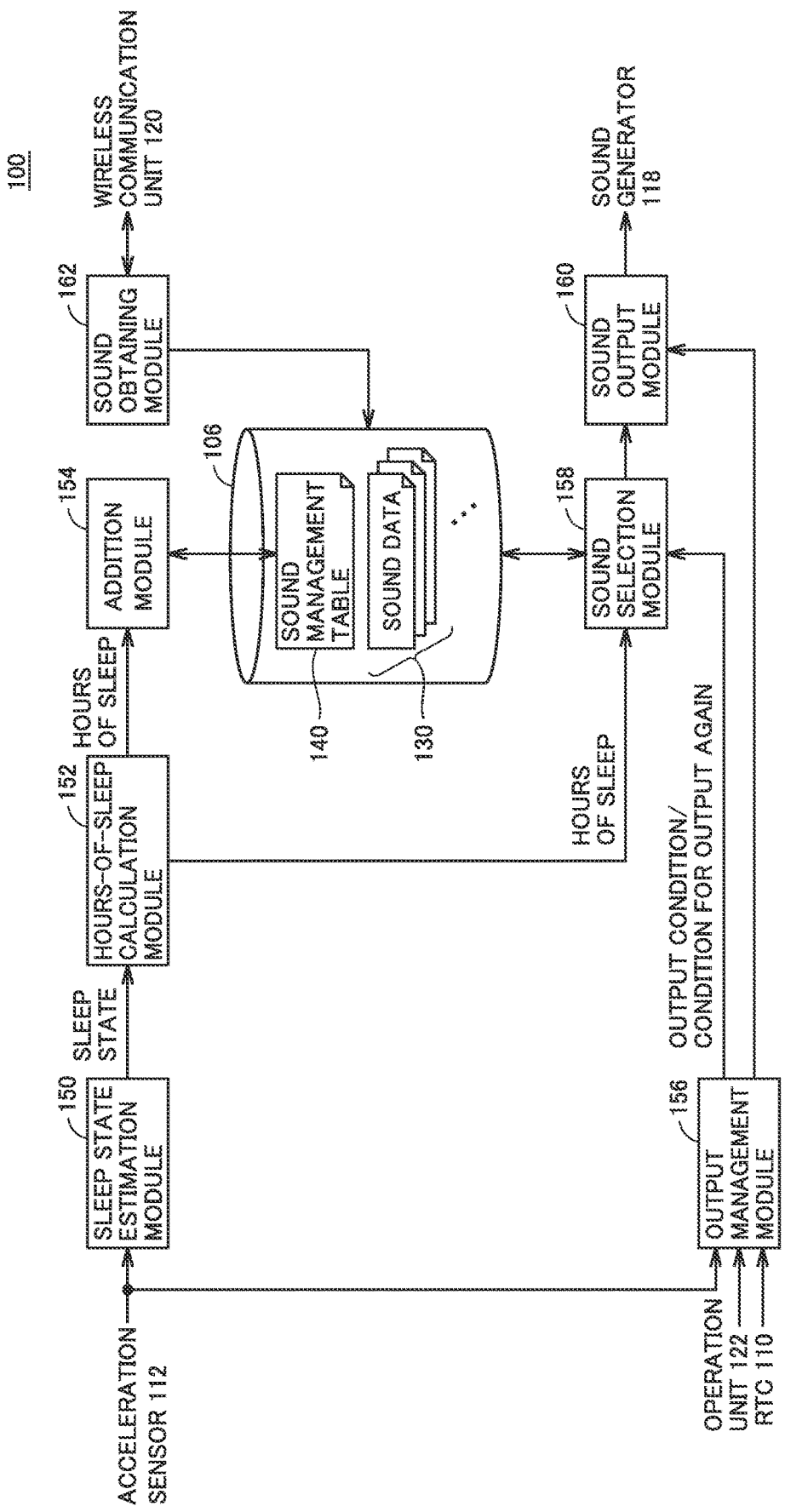
FIG. 5 shows an exemplary illustrative non-limiting drawing illustrating a functional configuration of the output apparatus according to the present embodiment.

FIG. 5 is a schematic diagram showing an exemplary functional configuration of output apparatus 100 according to the present embodiment. Referring to FIG. 5, output apparatus 100 includes, as its main functional components, a sleep state estimation module 150, an hours-of-sleep calculation module 152, an addition module 154, an output management module 156, a sound selection module 158, a sound output module 160, and a sound obtaining module 162. These functional components are typically implemented by execution of system program 108 by processor 102 of output apparatus 100.

Sleep state estimation module 150 estimates a sleep state of a user based on a result of measurement by a sensor that measures body motion of the user. For example, acceleration sensor 112 measures body motion of the user. Typically, output apparatus 100 is arranged on bedclothes (a mattress or the like) on which the user lies, so as to detect body motion produced by the user during sleep.

The sleep state estimated by sleep state estimation module 150 may include, for example, a sleeping state and an awake (awakened) state. The sleeping state may further be divided into REM sleep and non-REM sleep, or depth of sleep may be outputted. Sleep state estimation module 150 may estimate the sleep state and output a result of estimation only when body motion of the user is successfully appropriately measured. For example, when the user is not present within a range of measurement or when the user is not ready to lie on bed, output of a result of estimation of the sleep state may not be provided.

Without being limited to acceleration sensor 112, another sensor may be used to measure body motion of the user and to estimate the sleep state of the user. Any known algorithm can be adopted as an algorithm for estimating the sleep state of the user.

Hours-of-sleep calculation module 152 calculates hours of sleep of the user based on the sleep state of the user estimated by sleep state estimation module 150. More specifically, hours-of-sleep calculation module 152 integrates time periods during which the user is sleeping in the sleep states of the user successively outputted from sleep state estimation module 150. Hours-of-sleep calculation module 152 outputs as the hours of sleep of the user, for example, a cumulative total of the hours of sleep (from any initial state) and/or the hours of sleep during a prescribed most recent period (for example, twenty-four hours or one week).

Addition module 154 adds a new sound as the sound candidate group based on the calculated hours of sleep of the user. In the present embodiment, by way of example, the sound candidate group is managed with the use of sound management table 140. More specifically, in sound management table 140, a plurality of identifiers are defined, and one or more pieces of sound data 130 are associated with each identifier. Furthermore, information indicating availability is added to each of the identifiers in sound management table 140. Addition module 154 adds a new sound as the sound candidate group by updating the information included in sound management table 140 that indicates availability. Details of management of the sound candidate group with the use of sound management table 140 will be described later.

Output management module 156 determines whether or not an output condition has been satisfied. When output apparatus 100 is implemented as an alarm clock, output management module 156 determines whether or not start time set in advance has come based on current time provided by RTC 110. For example, the user may be able to freely set the start time by operating output apparatus 100 and/or portable terminal 200.

Thus, the output condition may include arrival of start time set in advance. When the user's sleep is shallow at the time when start time set in advance is close, the output condition may be determined as being satisfied.

Sound selection module 158 selects a sound to be outputted from the sound candidate group. Details of a method of selection of a sound by sound selection module 158 will be described later.

Sound output module 160 outputs the selected sound when the output condition is satisfied. More specifically, when output management module 156 determines that the output condition has been satisfied, sound output module 160 reproduces sound data 130 corresponding to the sound selected by sound selection module 158. Sound generator 118 generates a sound in accordance with a signal generated by reproduction of sound data 130.

Sound obtaining module 162 obtains a sound from another information processing apparatus (for example, portable terminal 200) different from output apparatus 100. More specifically, sound obtaining module 162 communicates with portable terminal 200 through wireless communication unit 120 to obtain new sound data 130 and has the new sound data stored in storage 106. An entry corresponding to the sound (sound data 130) obtained from portable terminal 200 is added to sound management table 140.

The sound (sound data 130) obtained from portable terminal 200 may or may not be added to the sound candidate group immediately after it is obtained.

E. Estimation of Sleep State and Calculation of Hours of Sleep

Details of estimation of the sleep state and calculation of hours of sleep of the user will now be described.

Sleep state estimation module 150 of output apparatus 100 estimates the sleep state of the user based on a result of measurement by the sensor that measures body motion of the user. Typically, the result of measurement by the sensor that measures body motion of the user is provided from acceleration sensor 112. Any known algorithm can be adopted as an algorithm for estimating the sleep state of the user based on the body motion of the user.

Figure 6:
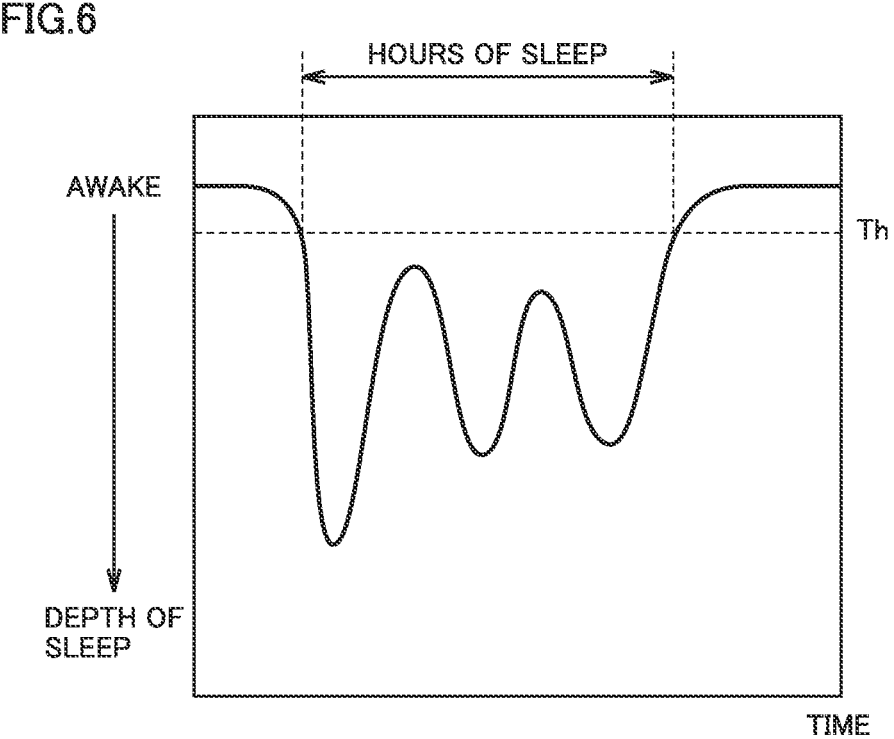
FIG. 6 shows an exemplary illustrative non-limiting drawing illustrating an exemplary sleep state estimated by the output apparatus according to the present embodiment.

FIG. 6 is a schematic diagram showing an exemplary sleep state estimated by output apparatus 100 according to the present embodiment. Referring to FIG. 6, sleep state estimation module 150 of output apparatus 100 outputs as a result of estimation of the sleep state, for example, an indicator indicating depth of sleep each time the user wakes up.

Hours-of-sleep calculation module 152 of output apparatus 100 can set a prescribed criterion value Th for the indicator indicating depth of sleep and calculate a period during which the depth of sleep exceeds criterion value Th as the hours of sleep of the user.

The hours of sleep of the user may be accumulated from any initial state or calculated for each prescribed most recent cycle (for example, twenty-four hours or one week).

Through the processing as described above, output apparatus 100 estimates the sleep state of the user and calculates the hours of sleep of the user.

F. Sound Addition Processing

Details of the sound addition processing will now be described. In the sound addition processing, a new sound is added to the sound candidate group based on the hours of sleep of the user.

(f1: Typical Exemplary Processing)

A cumulative total of the calculated hours of sleep of the user may be used as an exemplary condition for adding a sound. Specifically, a new sound may be added to the sound candidate group based on the cumulative total of the hours of sleep of the user.

FIG. 7 is a schematic diagram for illustrating an exemplary condition used in the sound addition processing according to the present embodiment. Referring to FIG. 7, a threshold value table 170 defines a plurality of cumulative totals of the hours of sleep of the user beyond which the sound addition processing is performed.

When the cumulative total of the calculated hours of sleep of the user reaches at least one of threshold values defined in threshold value table 170, addition module 154 of output apparatus 100 adds a new sound to the sound candidate group. In an example shown in FIG. 7, the sound addition processing may be performed each time the cumulative total of the hours of sleep reaches each of 10 hr, 20 hr, 40 hr, 80 hr, 200 hr, 500 hr, 1000 hr, A plurality of threshold values for performing the sound addition processing may thus be set. Addition module 154 of output apparatus 100 adds a new sound to the sound candidate group each time the cumulative total of the calculated hours of sleep of the user reaches at least one of the plurality of threshold values.

In an example where a plurality of threshold values are set, intervals between adjacent threshold values may be identical to or different from one another. In threshold value table 170 shown in FIG. 7, the intervals between adjacent threshold values are set to gradually increase.

More specifically, a difference (20 hr) between the second threshold value (20 hr) and the third threshold value (40 hr) included in threshold value table 170 is larger than a difference (10 hr) between the first threshold value (10 hr) and the second threshold value (20 hr). This is also applicable to subsequent threshold values. By thus setting the threshold values, immediately after start of use, a sound is soon added. Therefore, the user can use the information processing apparatus with enjoyment. In addition, since time until addition of all sounds can be longer, the user can use the information processing apparatus with enjoyment for a longer period of time.

Figure 8:
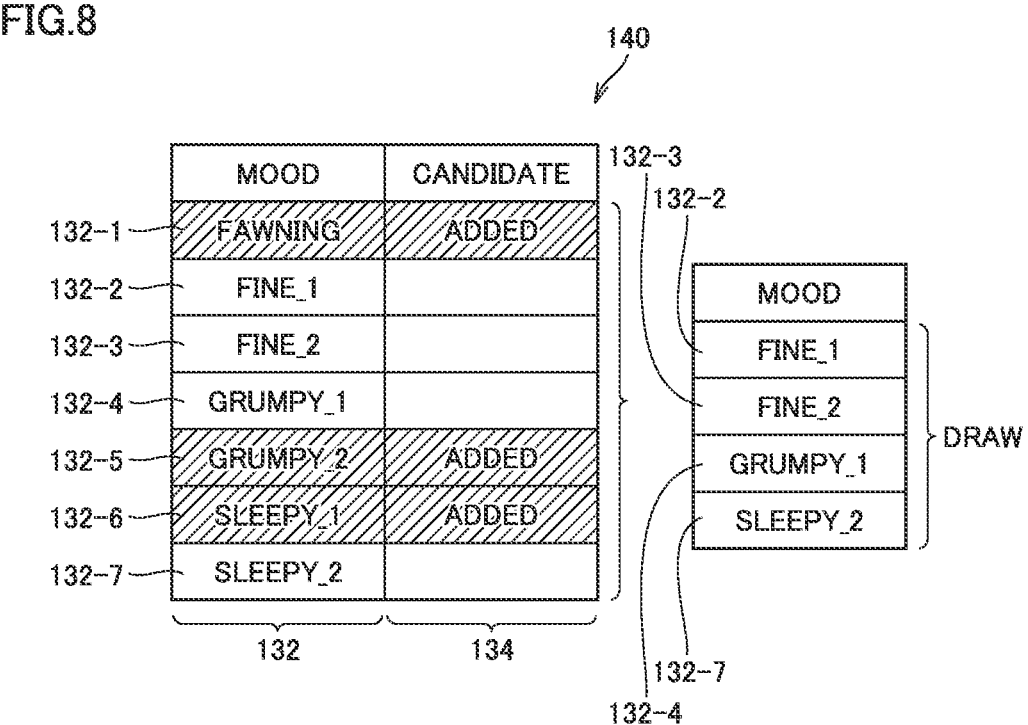
FIG. 8 shows an exemplary illustrative non-limiting drawing illustrating exemplary sound addition processing according to the present embodiment.

FIG. 8 is a schematic diagram for illustrating exemplary sound addition processing according to the present embodiment. Referring to FIG. 8, for example, it is assumed that sounds 132-1, 132-5, and 132-6 among sounds 132-1 to 132-7 have been added to sound candidate group 134.

In this case, sound 132 to be added to sound candidate group 134 is determined from sounds 132-2, 132-3, 132-4, and 132-7 which have not yet been added to sound candidate group 134.

A new sound to be added to sound candidate group 134 may be determined in a predetermined order. For example, sound 132 arranged at the top or the end among sounds 132-2, 132-3, 132-4, and 132-7 which have not yet been added to sound candidate group 134 may be determined as a new sound to be added to sound candidate group 134.

Alternatively, new sound 132 to be added to sound candidate group 134 may be determined by a draw. Specifically, addition module 154 of output apparatus 100 may determine new sound 132 to be added by the draw. For at least one sound 132, however, an order of addition thereof may be determined in advance, without the draw being made therefor. For example, sounds 132-1 to 132-6 among sounds 132-1 to 132-7 may randomly be added by the draw, whereas sound 132-7 may be added last without fail.

A probability that each of sounds 132 that have not yet been added to sound candidate group 134 is determined as new sound 132 may be equal. Specifically, a probability that each of sounds 132-2, 132-3, 132-4, and 132-7 shown in FIG. 8 is determined as a new sound to be added to sound candidate group 134 may be equal.

A probability of determination as a new sound to be added to sound candidate group 134 may be different based on the attribute of or additional information on sound 132.

Figure 9:
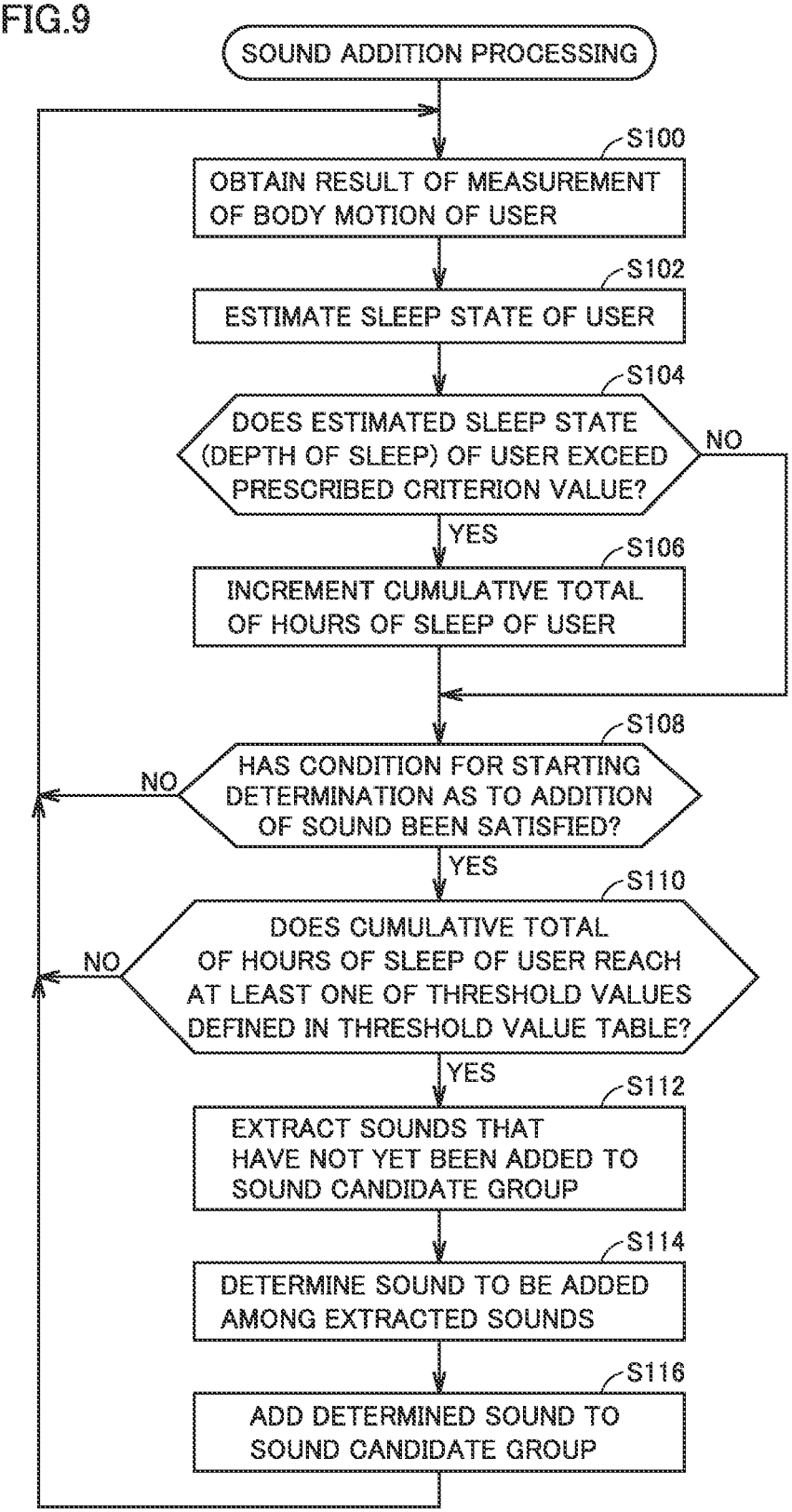
FIG. 9 shows an exemplary illustrative non-limiting flowchart illustrating a processing procedure in the sound addition processing according to the present embodiment.

FIG. 9 is a flowchart showing a processing procedure in the sound addition processing according to the present embodiment. Each step shown in FIG. 9 is typically performed by execution of system program 108 by processor 102 of output apparatus 100.

Referring to FIG. 9, output apparatus 100 obtains the result of measurement by the sensor that measures body motion of the user (step S100) and estimates the sleep state of the user (step S102). Output apparatus 100 determines whether or not the estimated sleep state (depth of sleep) of the user exceeds a prescribed criterion value (step S104).

When the estimated sleep state (depth of sleep) of the user exceeds the prescribed criterion value (YES in step S104), output apparatus 100 increments the cumulative total of the hours of sleep of the user (step S106). When the estimated sleep state (depth of sleep) of the user does not exceed the prescribed criterion value (NO in step S104), processing in step S106 is skipped.

Then, output apparatus 100 determines whether or not a condition for starting determination as to sound addition has been satisfied (step S108). For example, when the output apparatus can determine that the user has sufficiently been awake from the sleep state of the user, the condition for starting determination as to sound addition is satisfied.

When the condition for starting determination as to sound addition has not been satisfied (NO in step S108), subsequent processing is skipped and processing in step S100 or later is repeated.

When the condition for starting determination as to sound addition has been satisfied (YES in step S108), output apparatus 100 determines whether or not the cumulative total of the hours of sleep of the user has reached at least one of threshold values defined in threshold value table 170 (step S110). When the cumulative total of the hours of sleep of the user has reached none of the threshold values defined in threshold value table 170 (NO in step S110), subsequent processing is skipped and processing in step S100 or later is repeated.

When the cumulative total of the hours of sleep of the user has reached at least one of threshold values defined in threshold value table 170 (YES in step S110), output apparatus 100 extracts sounds 132 that have not yet been added to sound candidate group 134 (step S112) and determines sound 132 to be added among extracted sounds (step S114). Then, output apparatus 100 adds determined sound 132 to sound candidate group 134 (step S116). Then, processing in step S100 or later is repeated.

(f2: Determination as to Activation of Sound Addition Processing)

In the processing procedure shown in FIG. 9, though an example in which processing for adding a sound is performed when the cumulative total of the hours of sleep of the user has reached at least one of the threshold values defined in threshold value table 170 is shown, whether or not to perform processing for adding a sound may also be determined by a draw.

Specifically, output apparatus 100 may perform processing for determining whether or not to activate processing for adding new sound 132 to sound candidate group 134 based on the calculated hours of sleep of the user. In this case, sound 132 is added to sound candidate group 134 only when processing for adding new sound 132 is activated.

Figure 10:
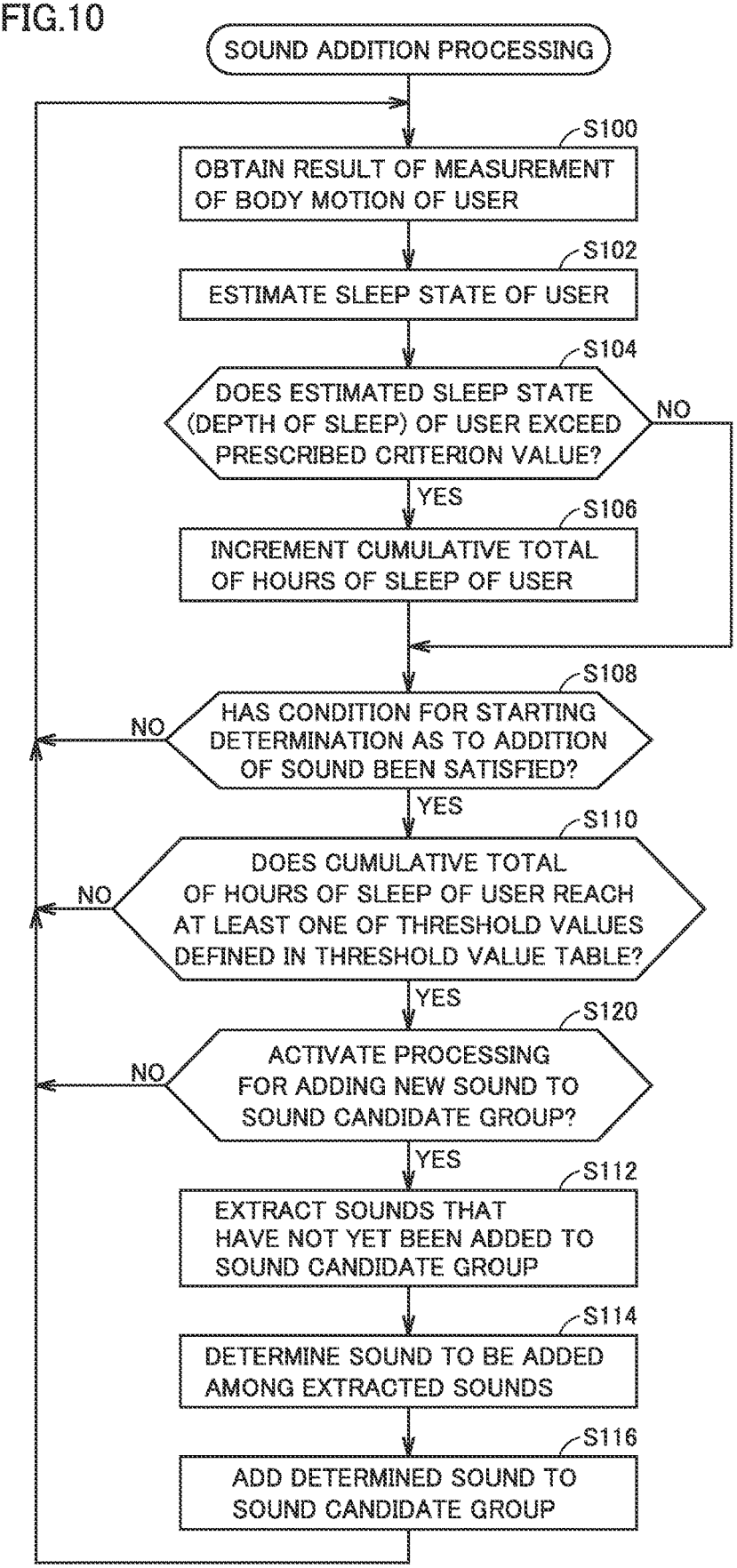
FIG. 10 shows an exemplary illustrative non-limiting flowchart illustrating another processing procedure in the sound addition processing according to the present embodiment.

FIG. 10 is a flowchart showing another processing procedure in the sound addition processing according to the present embodiment. As compared with the flowchart shown in FIG. 9, the flowchart shown in FIG. 10 additionally includes step S120 performed after step S110.

Specifically, when the cumulative total of the hours of sleep of the user has reached at least one of the threshold values defined in threshold value table 170 (YES in step S110), output apparatus 100 determines whether or not to activate processing for adding new sound 132 to sound candidate group 134 (step S120). Determination in step S120 may be made based on a length of the hours of sleep of the user during a prescribed most recent period or the cumulative total of the hours of sleep of the user, or alternatively by the draw. A probability in the draw may be varied based on the hours of sleep of the user. For example, the probability of activation (that is, the probability of permission) may be higher as the hours of sleep of the user are longer.

When it is determined to activate the processing for adding new sound 132 to sound candidate group 134 (YES in step S120), output apparatus 100 performs processing in step S112 or later. When it is determined not to activate the processing for adding new sound 132 to sound candidate group 134 (NO in step S120), subsequent processing is skipped and processing in step S100 or later is repeated.

Thus, when the processing for adding a new sound is activated, addition module 154 of output apparatus 100 adds new sound 132 to sound candidate group 134.

(f3: Exemplary Evaluation of Hours of Sleep of User)

Though an example in which the cumulative total of the hours of sleep of the user is used is mainly described above, without being limited as such, the "hours of sleep of the user" may be used in any manner in the processing for adding new sound 132 to sound candidate group 134.

For example, a point may be calculated based on hours of sleep for each prescribed period (for example, twenty-four hours or one week), and when the cumulative total of calculated points reaches a prescribed threshold value, new sound 132 may be added to sound candidate group 134.

More specifically, a point can be given in such a manner that, based on a length of the hours of sleep for each night, two points are given when the hours of sleep of the user are long, one point is given when the hours of sleep of the user are normal, and zero point is given when the hours of sleep of the user are short. The point may be given every night or in a unit of a week or a month.

When the cumulative total of points is used, instead of or in addition to processing in steps S106 and S110 shown in FIG. 9, processing for determining a point, processing for calculating the cumulative total of points, and processing for determining whether or not the cumulative total of points has reached a prescribed threshold value are performed.

Step S120 shown in FIG. 10 may be performed using points calculated based on the hours of sleep for each prescribed period. Specifically, whether or not to activate the processing for adding new sound 132 to sound candidate group 134 may be determined based on the calculated points.

Output apparatus 100 may thus perform an evaluation function after the user wakes up (gets up), to make an evaluation based on the calculated hours of sleep immediately before. The "hours of sleep immediately before" means time spent for one sleep (normally, sleep for one night) from determination that the user fell asleep until the user wakes up. Though the sleep may become shallow or the user may be awakened within one sleep, such a case is handled as one sleep in principle.

By making an evaluation after the user wakes up based on the hours of sleep immediately before, the hours of sleep of the user can substantially be evaluated every day. Addition module 154 of output apparatus 100 adds new sound 132 to sound candidate group 134 based on a result of evaluation with the evaluation function.

Processing for evaluating the hours of sleep of the user for each prescribed period described above can be adopted instead of or together with the processing using the cumulative total of the hours of sleep of the user.

G. Sound Selection and Output Processing

Details of the sound selection and output processing will now be described.

As described with reference to FIG. 4, in the sound selection and output processing, sound 132 to be outputted is selected from sound candidate group 134. Then, the selected sound is outputted.

(g1: Processing Procedure)

Figure 11:
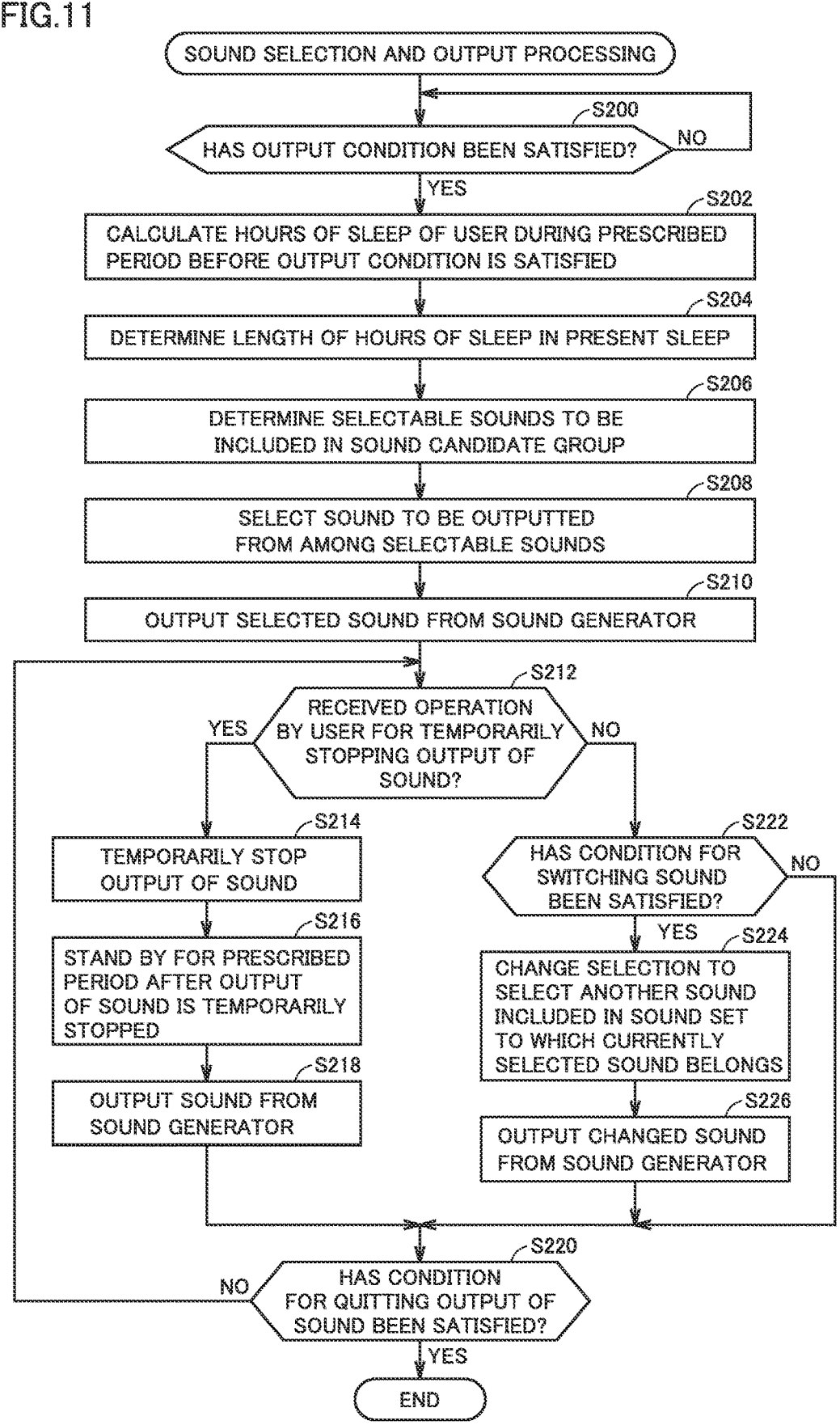
FIG. 11 shows an exemplary illustrative non-limiting flowchart illustrating a processing procedure in the sound selection and output processing according to the present embodiment.

FIG. 11 is a flowchart showing a processing procedure in the sound selection and output processing according to the present embodiment. Each step shown in FIG. 11 is typically performed by execution of system program 108 by processor 102 of output apparatus 100.

Referring to FIG. 11, output apparatus 100 determines whether or not the output condition has been satisfied (step S200). When the output condition has not been satisfied (NO in step S200), processing in step S200 is repeated.

The output condition typically means arrival of start time set in advance by the user (that is, set time to get up). When the user's sleep is shallow at the time when start time set in advance is close, the output condition may be determined as being satisfied.

When the output condition has been satisfied (YES in step S200), output apparatus 100 calculates hours of sleep of the user during a prescribed period before the output condition is satisfied (step S202).

The hours of sleep of the user during the prescribed period before the output condition is satisfied are counted based on the result of measurement by acceleration sensor 112. Therefore, the prescribed period may be, for example, a period until twelve hours before the set start time or a period from timing of determination that the user fell asleep until the start time.

Output apparatus 100 makes an evaluation based on the hours of sleep in the present sleep based on the calculated hours of sleep of the user during the prescribed period (step S204). For example, the hours of sleep of the user can be categorized into three types of "long", "normal", and "short". Processing in step S204 is performed as necessary and may be skipped as appropriate.

Then, output apparatus 100 determines selectable sounds 132 to be included in sound candidate group 134 (step S206). At this time, only at least one sound 132 to be included in sound candidate group 134 may be extracted as a choice based on the length of the hours of sleep in the present sleep. By thus changing the choices, as the hours of sleep are longer, a larger number of sounds 132 can be controlled to be the choices.

Output apparatus 100 selects sound 132 to be outputted from among selectable sounds 132 (step S208). Then, output apparatus 100 outputs selected sound 132 from sound generator 118 (step S210). Sound data 130 corresponding to selected sound 132 may repeatedly be reproduced.

After sound 132 is outputted, output apparatus 100 determines whether or not it has received an operation by the user for temporarily stopping output of sound 132 (step S212). The operation by the user for temporarily stopping output of sound 132 is, for example, an operation to activate a function referred to as snooze.

When output apparatus 100 receives the operation by the user for temporarily stopping output of sound 132 (YES in step S212), it temporarily stops output of sound 132 (step S214). Then, output apparatus 100 stands by for a prescribed period after output of sound 132 is temporarily stopped (step S216).

After stand-by for the prescribed period, output apparatus 100 outputs again sound 132 from sound generator 118 (step S218). When another sound 132 is included in the sound set to which currently selected sound 132 belongs, selection may be changed to select another sound 132.

Then, output apparatus 100 determines whether or not a condition for quitting output of sound 132 has been satisfied (step S220). When the condition for quitting output of sound 132 has not been satisfied (NO in step S220), processing in step S212 or later is repeated. When the condition for quitting output of sound 132 has been satisfied (YES in step S220), the process ends.

When output apparatus 100 has not received the operation by the user for temporarily stopping output of sound 132 (NO in step S212), it determines whether or not a condition for switching sound 132 has been satisfied (step S222). For example, when a duration of output of currently outputted sound 132 reaches a prescribed duration, the output apparatus may determine that the condition for switching sound 132 has been satisfied.

When the condition for switching sound 132 has been satisfied (YES in step S222), output apparatus 100 changes its selection to select another sound 132 included in the sound set to which currently selected sound 132 belongs (step S224) and outputs again changed sound 132 from sound generator 118 (step S226). Then, processing in step S220 is performed. Unless a plurality of sounds 132 are included in the sound set to which currently selected sound 132 belongs even when the condition for switching sound 132 has been satisfied, processing in steps S224 and S226 is skipped.

When the condition for switching sound 132 has not been satisfied (NO in step S222), processing in steps S224 and S226 is skipped.

In the processing procedure shown in FIG. 11, though exemplary processing for starting selection of sound 132 to be outputted when a condition for starting output of sound 132 (output condition) is satisfied is shown, the condition for starting output of sound 132 and the condition for starting selection of sound 132 may be set independently of each other. In other words, since sound 132 to be outputted should only be selected before start of processing for outputting sound 132, timing to select sound 132 may freely be determined.

(g2: Determination of Selectable Sounds (S206))

In a method of determining selectable sounds 132 in the processing procedure shown in FIG. 11, all sounds 132 that have been added to sound candidate group 134 may be set as choices.

Alternatively, only at least one sound 132 of sounds 132 that have been added to sound candidate group 134 may be set as a choice based on any information.

FIG. 12 is a schematic diagram for illustrating an exemplary method of determining selectable sounds 132 in output apparatus 100 according to the present embodiment. Referring to FIG. 12, sound management table 140 includes information as to whether or not a sound can be a choice (which is also referred to a "choice attribute" below) in addition to information on prepared sounds 132-1 to 132-7 and information as to whether or not each sound 132 has already been added to sound candidate group 134.

More specifically, sound management table 140 includes a choice attribute 136-1 when the hours of sleep in the present sleep are "long", a choice attribute 136-2 when the hours of sleep in the present sleep are "normal", and a choice attribute 136-3 when the hours of sleep in the present sleep are "short".

In an example shown in FIG. 12, selectable sounds 132 when the hours of sleep are "normal" are a subset of selectable sounds 132 when the hours of sleep are "long", and selectable sounds 132 when the hours of sleep are "short" are a subset of selectable sounds 132 when the hours of sleep are "long" and a subset of selectable sounds 132 when the hours of sleep are "normal". By adopting such relation of a set, the number of selectable sounds 132 when the hours of sleep are "long" can reliably be larger than the number of selectable sounds 132 when the hours of sleep are "normal" and "short". Such relation of a subset does not necessarily have to be maintained.

Output apparatus 100 makes an evaluation based on the hours of sleep in the present sleep (see step S204 in FIG. 11) and determines selectable sounds 132 by referring to choice attribute 136 corresponding to a result of evaluation.

Thus, when the calculated hours of sleep of the user exceed prescribed hours, sound selection module 158 of output apparatus 100 may select sound 132 to be outputted from among a larger number of sounds than when the calculated hours of sleep of the user do not exceed the prescribed hours.

(g3: Selection of Sound (S208))

In a method of selecting sound 132 in the processing procedure shown in FIG. 11, sound 132 to be outputted may be selected from among selectable sounds 132 in a predetermined order. Specifically, sound selection module 158 of output apparatus 100 may select sound 132 to be outputted in a predetermined order based on identifiers or the like of selectable sounds 132. By adopting such a method, the user can hear all sounds 132 included in sound candidate group 134.

A method of selecting sound 132 to be outputted from among selectable sounds 132 by the draw may be adopted as another method of selecting sound 132 to be outputted. Specifically, sound selection module 158 of output apparatus 100 selects sound 132 to be outputted from among selectable sounds 132 by the draw. By adopting such a method, the user can be given unexpectedness.

At this time, the probability of selection of sound 132 may be varied based on a result of evaluation based on the hours of sleep in the present sleep.

FIG. 13 is a schematic diagram for illustrating an exemplary method of selecting sound 132 in output apparatus 100 according to the present embodiment. Referring to FIG. 13, sound management table 140 includes information representing a probability of selection (which is also referred to a "selection probability setting" below) in addition to information on prepared sounds 132-1 to 132-7 and information as to whether or not each sound 132 has already been added to sound candidate group 134.

More specifically, sound management table 140 includes a selection probability setting 138-1 when the result of evaluation of the hours of sleep in the present sleep indicates "long", a selection probability setting 138-2 when the result of evaluation of the hours of sleep in the present sleep indicates "normal", and a selection probability setting 138-3 when the result of evaluation of the hours of sleep in the present sleep indicates "short". A value shown in selection probability setting 138 is a kind of a weight coefficient, and a larger value means a higher probability of selection.

In each of selection probability settings 138, the probability set for each sound 132 is not equal. For example, in selection probability setting 138-1, a higher probability of selection is set for "fine_1" and "fine_2" than other sounds 132 (mood). In selection probability setting 138-3, a higher probability is set for "grumpy_1", "grumpy_2", "sleepy_1", and "sleepy_2" than other sounds 132 (mood).

The probability that at least one sound 132 included in sound candidate group 134 is selected as sound 132 to be outputted may be different from the probability that another sound 132 included in sound candidate group 134 is selected as sound 132 to be outputted.

Output apparatus 100 makes an evaluation based on the hours of sleep in the present sleep (see step S204 in FIG. 11) and determines the probability of selection of each sound 132 included as the choice by referring to selection probability setting 138 corresponding to the result of evaluation. Then, output apparatus 100 selects sound 132 to be outputted by the draw, based on the determined probability of selection of each sound 132.

The probability (selection probability setting 138) that sound 132 included in sound candidate group 134 is selected as sound 132 to be outputted by the draw may thus be higher as the hours of sleep of the user during the prescribed period before the output condition is satisfied are longer.

In changing selectable sound 132 among sounds 132 included in sound candidate group 134 as shown in FIG. 12, by setting the probability of corresponding sound 132 in selection probability setting 138 shown in FIG. 13 to "zero", substantially the same result may be obtained.

FIG. 14 is a schematic diagram for illustrating another exemplary method of selecting sound 132 in output apparatus 100 according to the present embodiment. Referring to FIG. 14, the probability of sound 132 to be excluded from choices in each of selection probability settings 138-1, 138-2, and 138-3 is set to "zero". By adopting such selection probability setting 138, the choices can be different and the probability of selection of each sound 132 can also be different depending on the length of the hours of sleep in the present sleep.

In addition to setting of the probability of selection in advance for sound 132, the probability of selection may dynamically be varied. For example, selection of sound 132 shortly after addition thereof to sound candidate group 134 may be more likely. Specifically, sound 132 more recently added to sound candidate group 134 may be higher in probability of selection as sound 132 to be outputted. Furthermore, immediately after addition of new sound 132, that added new sound 132 may be selected without fail.

By thus setting the probability of selection, possibility that the user hears sound 132 soon after addition thereof to sound candidate group 134 can be made higher.

(g4: Change of Sound (S218 and S226))

Processing for changing the sound (S218 and S226) in the processing procedure shown in FIG. 11 will now be described.

Figure 15:
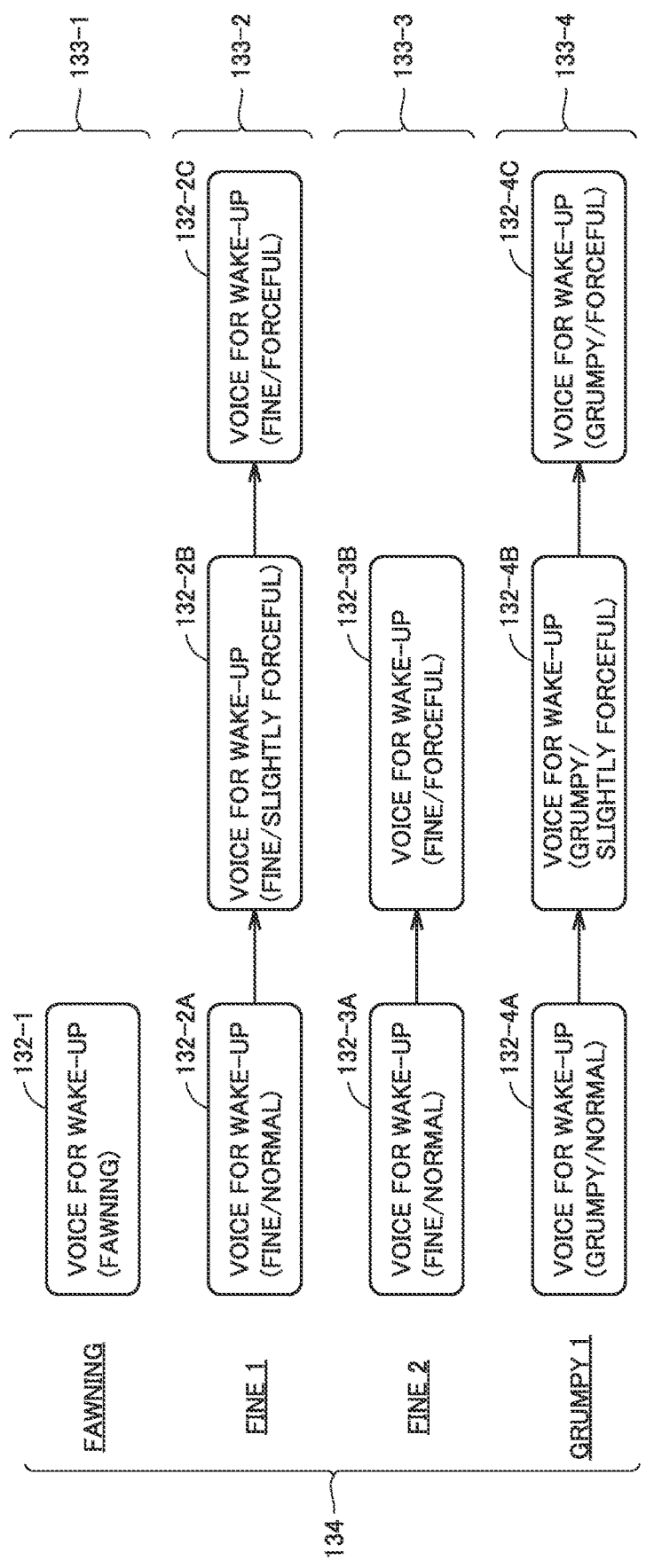
FIG. 15 shows an exemplary illustrative non-limiting drawing illustrating exemplary processing for changing a sound in the output apparatus according to the present embodiment.

FIG. 15 is a schematic diagram for illustrating exemplary processing for changing a sound in output apparatus 100 according to the present embodiment. Referring to FIG. 15, sounds 132 are added to sound candidate group 134 in a unit of a sound set 133 composed of a plurality of sounds 132.

In an example shown in FIG. 15, a sound set 133-1 composed of sound 132-1 is associated with the mood "fawning." A sound set 133-2 composed of sounds 132-2A, 132-2B, and 132-2C is associated with the mood "fine_1". A sound set 133-3 composed of sounds 132-3A and 132-3B is associated with the mood "fine_2". A sound set 133-4 composed of sounds 132-4A, 132-4B, and 132-4C is associated with the mood "grumpy_1".

Sounds 132 to be outputted are thus selected in a unit of sound set 133 from sound candidate group 134 shown in FIG. 15. Then, at least one of one or more sounds 132 included in selected sound set 133 is outputted. Specifically, sound selection module 158 of output apparatus 100 selects sounds 132 to be outputted in a unit of sound set 133 and determines sound 132 to be outputted from among sounds 132 included in selected sound set 133.

When sound set 133 includes a plurality of sounds 132, output apparatus 100 switches among sounds 132 to be outputted as appropriate in response to any switching condition being satisfied.

For example, when sound set 133 corresponding to "fine_1" has been selected, initially, a voice (sound 132-2A) for waking the user up is outputted in a tone giving a "fine" impression. When the switching condition is satisfied after output of sound 132-2A, switching to a voice (sound 132-2B) for waking the user up in a slightly forceful tone is made. Furthermore, when the switching condition is satisfied after output of sound 132-2B, switching to a voice (sound 132-2C) for waking the user up in a more forceful tone is made.

When the switching condition is satisfied after output of sound 132 is started, sound selection module 158 of output apparatus 100 thus selects sound 132 different from previously selected sound 132 as sound 132 to be outputted next, from among sounds 132 included in selected sound set 133.

The duration of output of currently outputted sound 132 reaching a prescribed duration may be adopted as the condition for switching sound 132 (step S224 in FIG. 11). Specifically, when output of sound 132 is not temporarily stopped (NO in S212 in FIG. 11), output of sound 132 continues. When the duration of output of sound 132 that is being output reaches the prescribed duration (for example, three minutes), a type of sound 132 to be outputted may be changed.

When a duration of reproduction of sound 132 is, for example, approximately several seconds, in order to continue output of sound 132, the same sound 132 is repeatedly reproduced. The number of times of repetition of this same sound 132 reaching a predetermined number of times may be set as the condition for switching of sound 132.

Temporary stop of output of sound 132 may be adopted as another condition for switching of sound 132. Output apparatus 100 may be able to temporarily stop output of sound 132 in response to an operation by the user (S212 and S214 in FIG. 11). In this case, the type of sound 132 to be outputted may be changed by being triggered by temporary stop of output of sound 132. Since output of sound 132 has temporarily been stopped, changed sound 132 is not actually outputted until a prescribed time period elapses and the output condition is satisfied again.

H. Processing for Output Again of Sound

Processing for outputting again previously outputted sound 132 will now be described.

Figure 16:
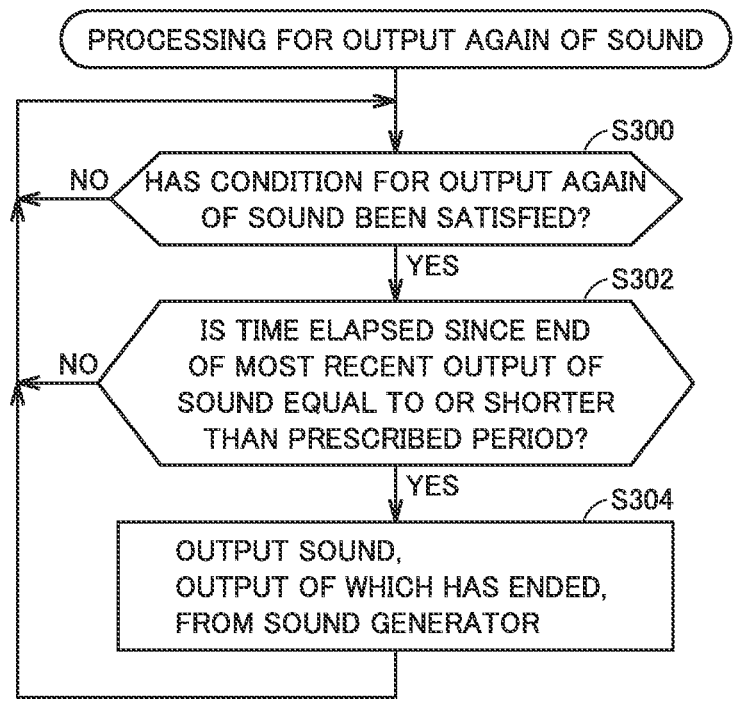
FIG. 16 shows an exemplary illustrative non-limiting flowchart illustrating a processing procedure for output again of a sound according to the present embodiment.

FIG. 16 is a flowchart showing a processing procedure for output again of a sound according to the present embodiment. Each step shown in FIG. 16 is typically performed by execution of system program 108 by processor 102 of output apparatus 100.

Referring to FIG. 16, output apparatus 100 determines whether or not a condition for output again of sound 132 has been satisfied (step S300). When the condition for output again of sound 132 has not been satisfied (NO in step S300), processing in step S300 or later is repeated.

When the condition for output again of sound 132 has been satisfied (YES in step S300), output apparatus 100 determines whether or not time elapsed since end of most recent output of sound 132 is equal to or shorter than a prescribed period (step S302). When time elapsed since end of most recent output of sound 132 is longer than the prescribed period (NO in step S300), processing in step S300 or later is repeated.

When the time elapsed since end of most recent output of sound 132 is equal to or shorter than the prescribed period (YES in step S302), output apparatus 100 outputs sound 132, output of which has ended, from sound generator 118 (step S304). In step S304, basically, sound data 130 corresponding to sound 132, output of which has ended, is reproduced once. Then, processing in step S300 or later is performed.

When the condition for output again is satisfied within the prescribed period after end of output of sound 132, sound output module 160 of output apparatus 100 outputs again sound 132, output of which has ended.

Reception of an operation by the user may be adopted as the condition for output again. Specifically, reception of an operation by the user onto operation unit 122 of output apparatus 100 or shaking of output apparatus 100 by the user may be adopted as the condition for output again.

For example, a shake that occurs in output apparatus 100 can be sensed based on a result of measurement from acceleration sensor 112. The condition for output again may thus include sensing of a shake of output apparatus 100.

I. Other Embodiments

Though an exemplary configuration for output of a sound has been described, light or vibration may be outputted in addition to or instead of the sound. In this case as well, similarly to the sound, variation of outputted light or vibration may sequentially be added.

While certain example systems, methods, devices and apparatuses have been described herein, it is to be understood that the appended claims are not to be limited to the systems, methods, devices and apparatuses disclosed, but on the contrary, are intended to cover various modifications and equivalent arrangements included within the spirit and scope of the appended claims.

What is claimed is:

1. An information processing apparatus comprising:
a memory storing a computer-readable program; and
one or more processors that, when executing the computer-readable program, perform:
selecting a sound to be outputted from a sound candidate group,
outputting the selected sound when an output condition is satisfied,
estimating a sleep state of a user based on a result of measurement by a sensor configured to measure body motion of the user,
calculating hours of sleep of the user based on the estimated sleep state of the user, and
adding a new sound to the sound candidate group based on the calculated hours of sleep of the user.

2. The information processing apparatus according to claim 1, wherein the adding the new sound to the sound candidate group is based on a cumulative total of the calculated hours of sleep of the user.

3. The information processing apparatus according to claim 2, wherein the adding the new sound to the sound candidate group comprises adding the new sound when the cumulative total of the calculated hours of sleep of the user reaches a prescribed threshold value.

4. The information processing apparatus according to claim 3, wherein
the prescribed threshold value comprises a plurality of threshold values, and
the adding the new sound to the sound candidate group comprises adding the new sound each time the cumulative total of the calculated hours of sleep of the user reaches a threshold value of the plurality of threshold values.

5. The information processing apparatus according to claim 4, wherein as compared with a difference between a first threshold value included in the plurality of threshold values and a second threshold value largest next to the first threshold value, a difference between the second threshold value and a third threshold value largest next to the second threshold value is larger.

6. The information processing apparatus according to claim 1, wherein
the one or more processors, when executing the computer-readable program, further perform, after the user wakes up, evaluation based on the calculated hours of sleep immediately before, and
the adding the new sound to the sound candidate group comprises adding the new sound based on a result of the evaluation.

7. The information processing apparatus according to claim 1, wherein the adding the new sound to the sound candidate group comprises determining the new sound to be added by a draw.

8. The information processing apparatus according to claim 7, wherein a probability that each of sounds that have not yet been added to the sound candidate group is determined as the new sound is equal.

9. The information processing apparatus according to claim 1, wherein
the one or more processors, when executing the computer-readable program, further perform determining whether to activate processing for adding a new sound to the sound candidate group based on the calculated hours of sleep of the user, and
the adding the new sound to the sound candidate group comprises adding the new sound to the sound candidate group when processing for adding the new sound is activated.

10. The information processing apparatus according to claim 1, wherein the selecting a sound comprises selecting a sound to be outputted from the sound candidate group by a draw.

11. The information processing apparatus according to claim 10, wherein the one or more processors, when executing the computer-readable program, further perform determining one or more selectable sounds from sounds included in the sound candidate group based on the hours of sleep of the user immediately before the output condition is satisfied.

12. The information processing apparatus according to claim 11, wherein the selecting the sound comprises selecting, when the calculated hours of sleep of the user exceed prescribed hours, a sound to be outputted from among more sounds than when the calculated hours of sleep of the user do not exceed the prescribed hours.

13. The information processing apparatus according to claim 11, wherein a probability that at least one sound included in the sound candidate group is selected as the sound to be outputted is higher as the hours of sleep of the user are longer.

14. The information processing apparatus according to claim 11, wherein a probability that each of sounds included in the sound candidate group is selected as the sound to be outputted is equal.

15. The information processing apparatus according to claim 11, wherein a sound more recently added to the sound candidate group is higher in probability of selection as the sound to be outputted.

16. The information processing apparatus according to claim 1, wherein the selecting a sound comprises selecting the sound to be outputted in a predetermined order from the sound candidate group.

17. The information processing apparatus according to claim 1, wherein
a sound is added to the sound candidate group in a unit of a sound set composed of a plurality of sounds, and
the selecting a sound comprises selecting sounds to be outputted in the unit of the sound set and determining a sound to be outputted from among the sounds included in the selected sound set.

18. The information processing apparatus according to claim 17, wherein the selecting the sound comprises selecting as a sound to be outputted next, a sound different from a previously selected sound from among the sounds included in the sound set when a switching condition is satisfied after output of the sound is started.

19. The information processing apparatus according to claim 18, wherein the switching condition comprises a condition that a duration of output of a sound that is currently being outputted reaches a prescribed duration.

20. The information processing apparatus according to claim 18, wherein
the one or more processors, when executing the computer-readable program, further perform temporarily stopping output of the sound, and
the switching condition comprises temporary stop of output of the sound.

21. The information processing apparatus according to claim 1, wherein the outputting the sound comprises outputting again the sound, output of which has ended, when a condition for output again is satisfied within a prescribed period after end of output of the sound.

22. The information processing apparatus according to claim 21, wherein
the one or more processors, when executing the computer-readable program, further perform sensing a shake that occurs in the information processing apparatus, and
the condition for output again comprises sensing of the shake of the information processing apparatus.

23. The information processing apparatus according to claim 1, wherein the sensor comprises an acceleration sensor.

24. The information processing apparatus according to claim 1, wherein the one or more processors, when executing the computer-readable program, further perform obtaining a sound from another information processing apparatus different from the information processing apparatus.

25. A sound-generating system, comprising:
a memory and at least one processor configured to perform operations comprising:
selecting, from a sound candidate group, a sound to be outputted;
causing the selected sound to be outputted when an output condition is satisfied;
estimating a sleep state of a user based on a result of measurement by a sensor configured to measure body motion of the user;
calculating hours of sleep of the user based on the estimated sleep state of the user; and
adding a new sound to the sound candidate group based on the calculated hours of sleep of the user.

26. A non-transitory computer-readable storage medium with an executable program stored thereon, the program when executed causing a computer configured to output a sound to perform:
selecting a sound to be outputted from a sound candidate group;
outputting the selected sound when an output condition is satisfied;
estimating a sleep state of a user based on a result of measurement by a sensor configured to measure body motion of the user;
calculating hours of sleep of the user based on the estimated sleep state of the user; and
adding a new sound to the sound candidate group based on the calculated hours of sleep of the user.

27. A method performed in an information processing apparatus configured to output a sound, the method comprising:
selecting a sound to be outputted from a sound candidate group;
outputting the selected sound when an output condition is satisfied;
estimating a sleep state of a user based on a result of measurement by a sensor that measures body motion of the user;
calculating hours of sleep of the user based on the estimated sleep state of the user; and
adding a new sound to the sound candidate group based on the calculated hours of sleep of the user.

* * * * *